United States Patent
Virag et al.

(10) Patent No.: US 7,948,676 B2
(45) Date of Patent: May 24, 2011

(54) AUTOMATED CASSETTE AND SLIDE HANDLING SYSTEM FOR AN AUTOMATIC MICROSCOPE

(75) Inventors: Tibor Virag, Budapest (HU); Yash Agarwal, New Haven, CT (US); Wei Guo, Unionville, CT (US); Richard Eberle, Wolcott, CT (US); Youngmin Kim, Wallingford, CT (US); Michael Kilpatrick, West Hartford, CT (US); Petros Tsipouras, Madison, CT (US); Triantafyllos Tafas, Rocky Hill, CT (US)

(73) Assignee: Ikonisys, Inc., New Haven, CT (US)

( * ) Notice: Subject to any disclaimer, the term of this patent is extended or adjusted under 35 U.S.C. 154(b) by 392 days.

(21) Appl. No.: 11/833,517

(22) Filed: Aug. 3, 2007

(65) Prior Publication Data

US 2008/0317566 A1   Dec. 25, 2008

Related U.S. Application Data

(60) Provisional application No. 60/821,545, filed on Aug. 4, 2006.

(51) Int. Cl.
   *G02B 21/26* (2006.01)
(52) U.S. Cl. .......................... 359/391; 359/368; 359/900
(58) Field of Classification Search .................. 359/368, 359/391–398
   See application file for complete search history.

(56) References Cited

U.S. PATENT DOCUMENTS

| | | | |
|---|---|---|---|
| 4,367,915 A | 1/1983 | Georges | |
| 5,215,317 A | 6/1993 | Jordan et al. | |
| 5,386,318 A * | 1/1995 | Kuhnert et al. | 359/394 |
| 6,847,481 B1 | 1/2005 | Ludl et al. | |
| 6,905,300 B1 | 6/2005 | Russum | |

OTHER PUBLICATIONS

U.S. Appl. No. 60/821,545, filed Aug. 4, 2006, Virag.

* cited by examiner

*Primary Examiner* — Thong Nguyen
(74) *Attorney, Agent, or Firm* — Kelley Drye & Warren

(57) ABSTRACT

An automated cassette and slide handling system is disclosed which organizes microscope slides in cassettes, automatically and sequentially removes individual slides from their respective cassettes, positioned each slide under the microscope as provided by the protocol, and after examination returns the slide to its proper cassette.

2 Claims, 8 Drawing Sheets

AUTOMATED CASSETTE AND SLIDE HANDLING SYSTEM FOR AN AUTOMATIC MICROSCOPE

CROSS REFERENCE TO RELATED APPLICATIONS

This application claims priority from U.S. Provisional Application No. 60/821,545, filed Aug. 4, 2006. All references cited in this specification, and their references, are incorporated by reference herein where appropriate for teachings of additional or alternative details, features, and/or technical background.

BACKGROUND OF THE INVENTION

1. Field of the Invention

The present invention generally relates to a system for organizing microscope slides in cassettes, automatically transferring the slides individually and in sequence into an automated microscope thus allowing each slide to be examined and analyzed, and subsequently retrieving each slide from the microscope and returning it to the originating cassette.

2. Summary of the Invention

In embodiments there is disclosed:

A mechanism for removing and replacing a slide housed in a cassette defining a plurality of slots configured for holding slides in spaced parallel configuration, the mechanism comprising:

a feed arm containing a longitudinal channel there through;

a longitudinal draw-out spring wire surrounding an imaginary longitudinal axis having a first end and a second end, the first and second end being bent orthogonal to one another and to the imaginary longitudinal axis of the draw-out spring wire, the longitudinal draw-out spring wire being positioned in the longitudinal channel in the feed arm such that bent ends protrude from the channel and wherein the longitudinal draw-out spring wire is operatively positioned in the longitudinal channel such that the draw-out spring wire is rotatable therein, allowing for each bent end to change orientation in respect to the feed arm.

A slide magazine cassette for storing microscope slides, the magazine comprising:

a housing comprising a top surface, a bottom surface, and two side surfaces, the surfaces defining a through-void there between;

a plurality of paired engagement structures attached to each of the side surfaces of the housing and projecting into the thorough-void, each of the paired engaging structures being substantially parallel to another pair of engaging structures attached to the antipodal side surface wherein the each of the parallel paired engaging structures is configured and spaced to allow for the engagement and support of a single microscope slide between the engaging structures, and to permit movement of the slide with respect to the engagement structures when a force is applied perpendicular to a parallel pair of engagement structures from either side of the through-void.

A microscope cassette handling system comprising:

a cassette defining a plurality of slots configured for holding microscope slides in a spaced parallel formation; to an elevator housing having a bottom wall and two-side walls, the walls defining a void configured to permit the cassette to be positioned therein;

an elevator control mechanism operatively connected to the elevator housing, the elevator control mechanism being operatively configured to raise and lower the elevator housing along a vertical axis;

a cassette unloading mechanism, the unloading mechanism being operatively configured to unload the cassette from the elevator housing; and a controller operatively connected to the cassette unloading mechanism and the elevator control mechanism, the controller configured to control the cassette unloading mechanism to unload the cassette from the elevator housing after one or more microscope slides have been dispensed from the cassette.

A method for automatically handling microscope slides stored in a series of ports within a cassette, the cassette having incorporated therewith a detectable device, in a system having an cassette input port, a cassette exit port, a cassette slide removal assembly, and a slide stage, the method comprising the steps of:

receiving the cassette having the slides at the input port;

detecting the cassette at the input port by sensing the detectable device;

automatically removing one of the microscope slides from a port in the cassette and placing the microscope slide onto the slide stage;

automatically removing the microscope slide from the slide stage and repositioning the slide in the port from which it was removed; and exporting the cassette from the exit port after one or more the microscope slides has been removed from the cassette and repositioned in the port from which it was removed.

BRIEF DESCRIPTION OF DRAWINGS

The embodiments are described with the aid of the following drawings.

DETAILED DESCRIPTION OF THE INVENTION

In an embodiment disclosed, the automated slide and cassette handling system includes: 1) cassette 100, 2) the cassette handler, 3) the slide handler assembly, and 4) slide holder stage 290.

Figure 1:
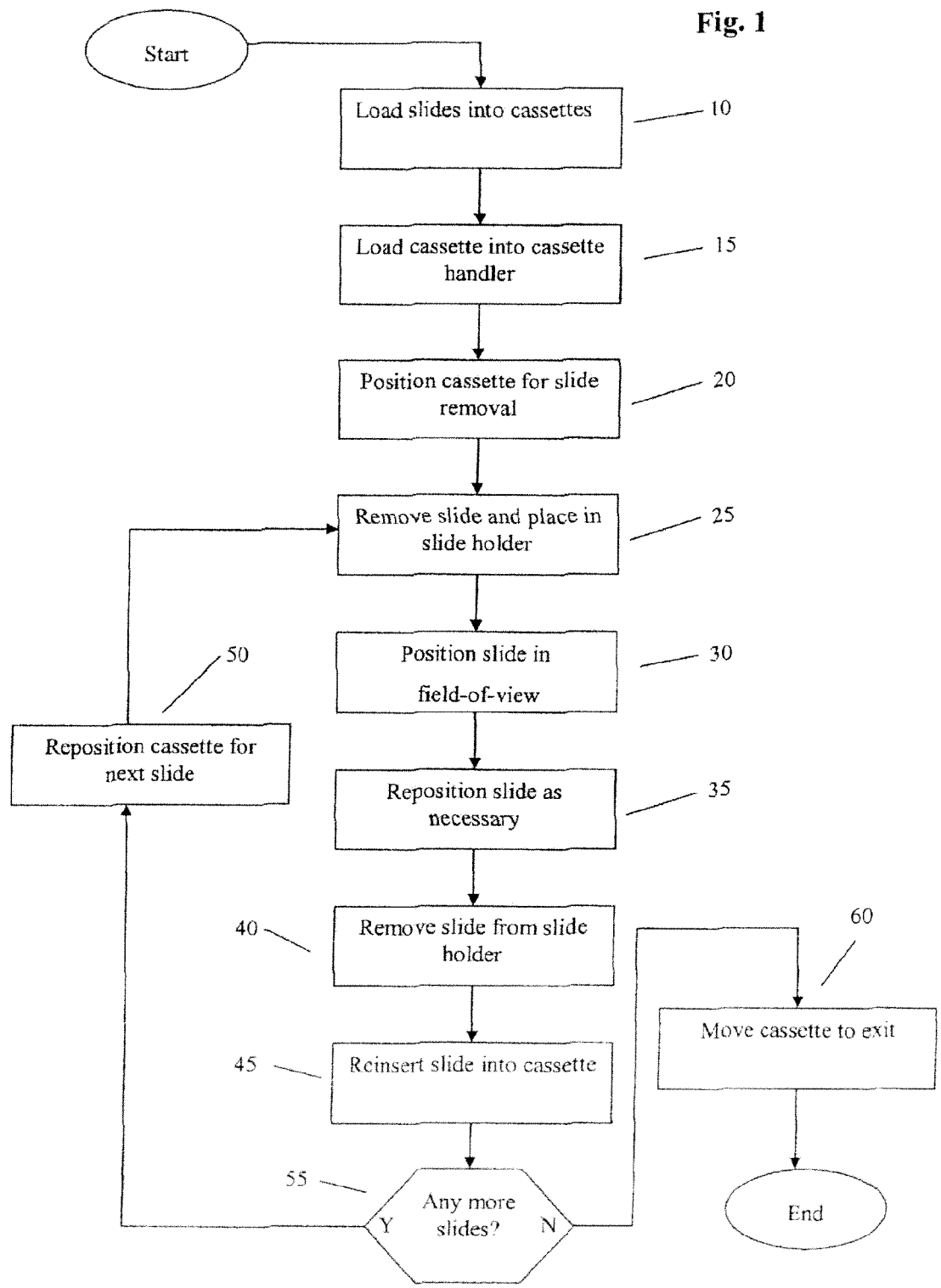
FIG. 1 is a simplified algorithmic flow chart schematically describing the sequence of events of an embodiment.
Figure 2:
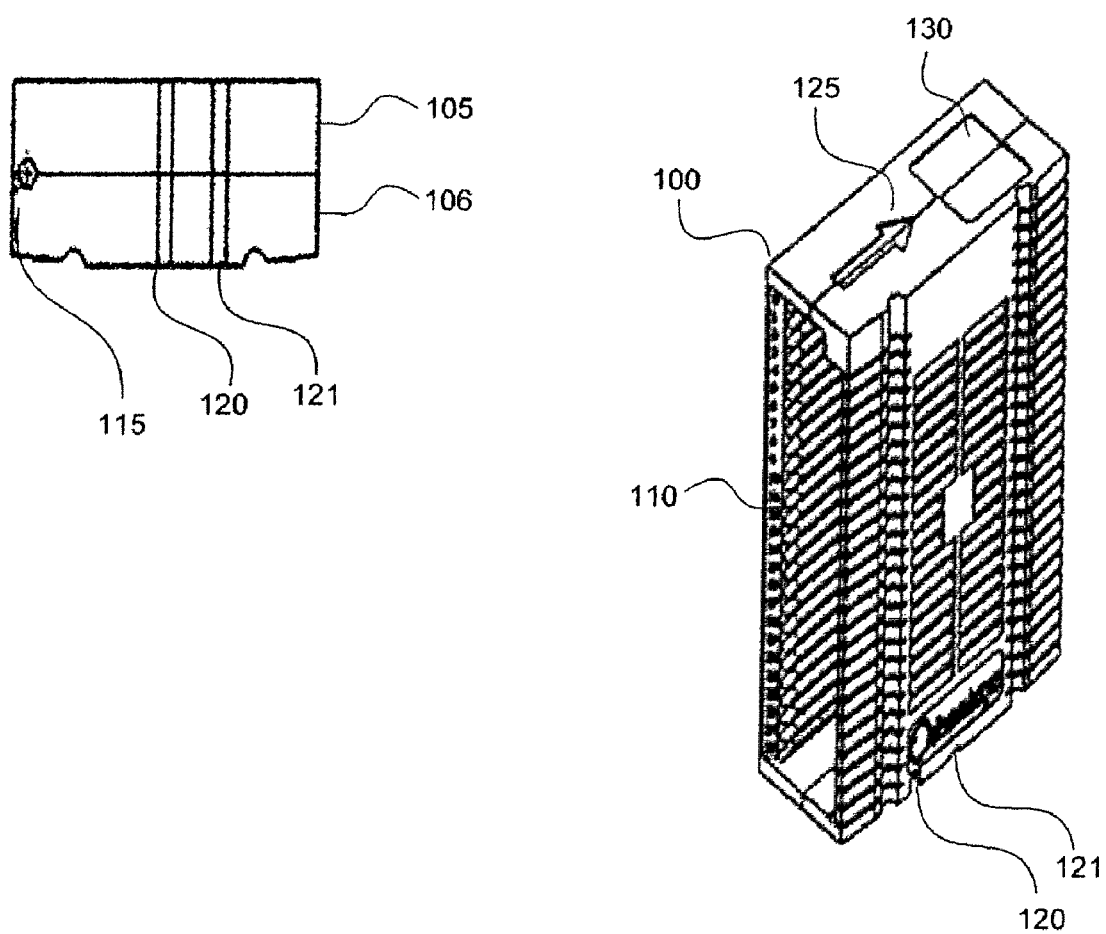
FIG. 2 is a simplified drawing of the microscope slide holding cassette.
Figure 9:
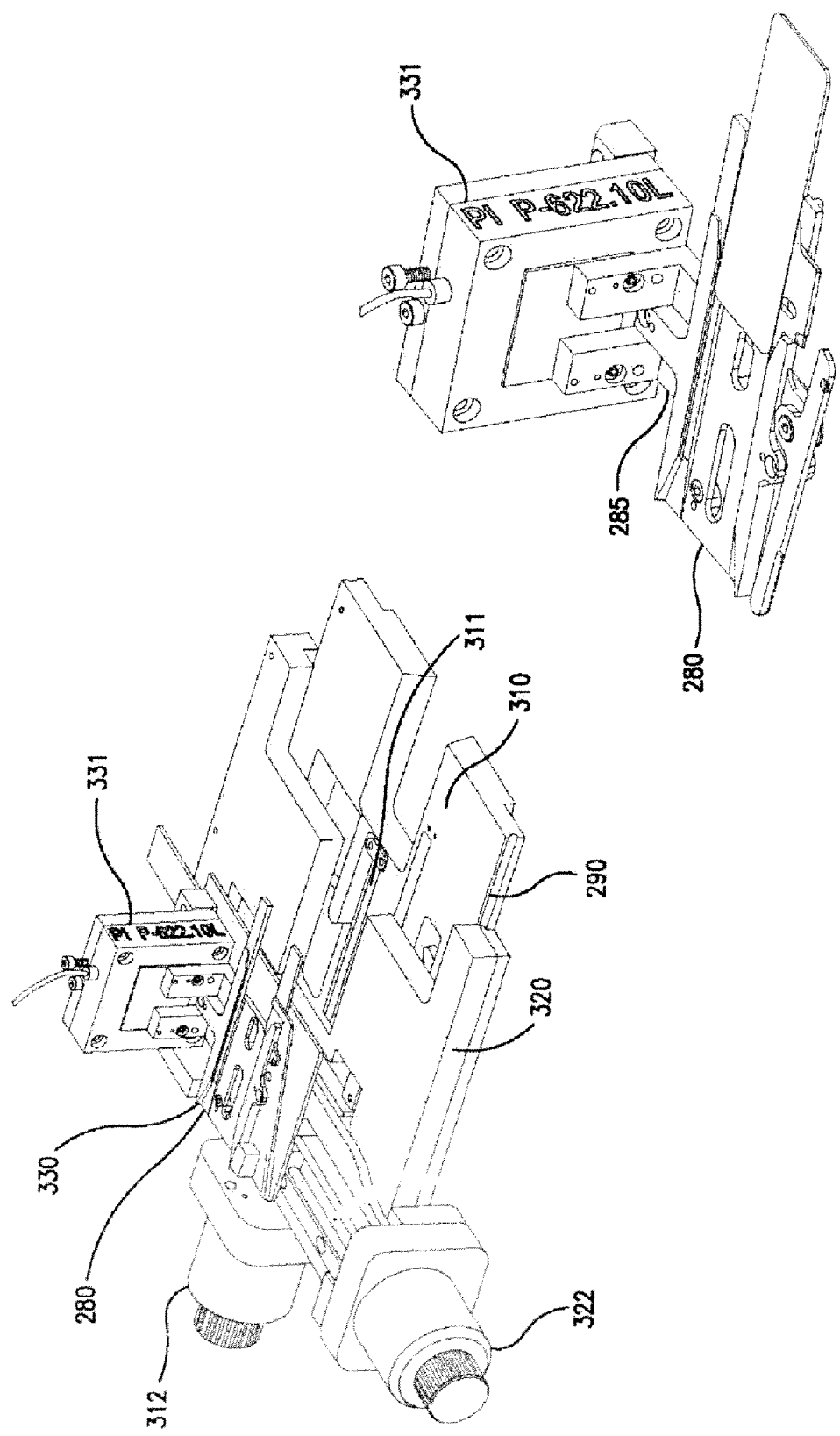
FIG. 9 illustrates an embodiment of the Z axis stage and slide holder mounted on the Y axis slide stage.

As shown in FIG. 1, individual prepared slides are loaded 10 into cassettes 100 (FIG. 2). In an embodiment, each cassette 100 has a capacity of 26 slides (of course more or less may be held). In operation, cassettes 100 are loaded into cassette handler 15 which positions 20 the cassette so that the first microscope slide may be removed from cassette 100 by the slide handler. The slide handler removes the slide and places it into slide holder 25 which is held by the slide holder stage 290 (FIG. 9). Slide holder stage 290 places the slide in the field of view of the microscope 30. During the microscopic examination, as determined by the protocol, slide holder stage 290 may reposition 35 the slide in the X, Y and Z Cartesian axis. After the microscopic examination has been completed, the slide handler removes 40 the slide from the slide holder. The slide handler then reinserts 45 the slide in cassette 100. The cassette handler repositions 50 cassette 100 so that the slide handler may access the next slide. The process is repeated 55 until all of the slides in the cassette 100 have been examined. Cassette 100 is next moved 60 to the output port for removal and next cassette 100 is positioned for access.

In an embodiment shown in FIG. 2, cassette 100 is a rectangular cartridge that holds microscope slides, which are to be examined. Cassette 100 may be implemented as a right plastic half 105 and a left plastic half 106, which are affixed together. Each cassette 100 has multiple slots 110 to hold the microscope slides. In an embodiment, 26 slots are available where the slots are numbered from 1 to 25 from bottom to top with the 26$^{th}$ slot named as C for the control slide. Thus, each cassette 100 can hold up to 25 patient slides.

Each of the slots of cassette 100 has a means for retaining the slide when it is installed into cassette 100, regardless of the orientation. In an embodiment, each slot has spring like fingers at the two ends. This is a unique feature of cassette 100 that enables secure slide holding when transporting slides in the cassette 100. This feature also makes cassette 100 suitable as a slide storage container.

Each cassette 100 includes a detectable device that allows an external sensor, mounted on cassette handler 200, to detect the presence of the cassette 100. In an embodiment, the detectable device is a circular magnet 115 inserted at the bottom of each cassette 100 so that an external magnetic sensor 215 may detect the presence of cassette 100. Additionally or alternatively, other types of detectable devices such as optical or radio frequency identification (RFID) tags may be employed for this function. Additional sensors may be incorporated to interrogate these tags thereby recovering recorded identification data.

In an embodiment, cassette 100 has two guides on the bottom surface. The first of these guides 120 permits the secure engagement of cassette 100 by a conveyor belt. The second guide 121 serves to accommodate an orientation pin that insures that cassette 100 is loaded into the cassette handler in the correct direction.

A visual indication of the correct orientation of cassette 100 when loading into the microscope system is located on the exterior of cassette 100. In an embodiment, the visual indication may be arrow 125 on the top of cassette 100. In addition, at a standardized location on the exterior of cassette 100, there is a rectangular area 130 reserved for a barcode label that uniquely identifies cassette 100. Alternatively, other labeling means such as textual or RFID tag may be utilized.

Cassette 100 incorporates a means whereby it may be fastened to a mechanism for positioning cassette 100 for automated slide removal. In an embodiment the fastening means may be two slots (not shown), which receive corresponding hooks extending from the cassette handler mechanism.

Figure 3:
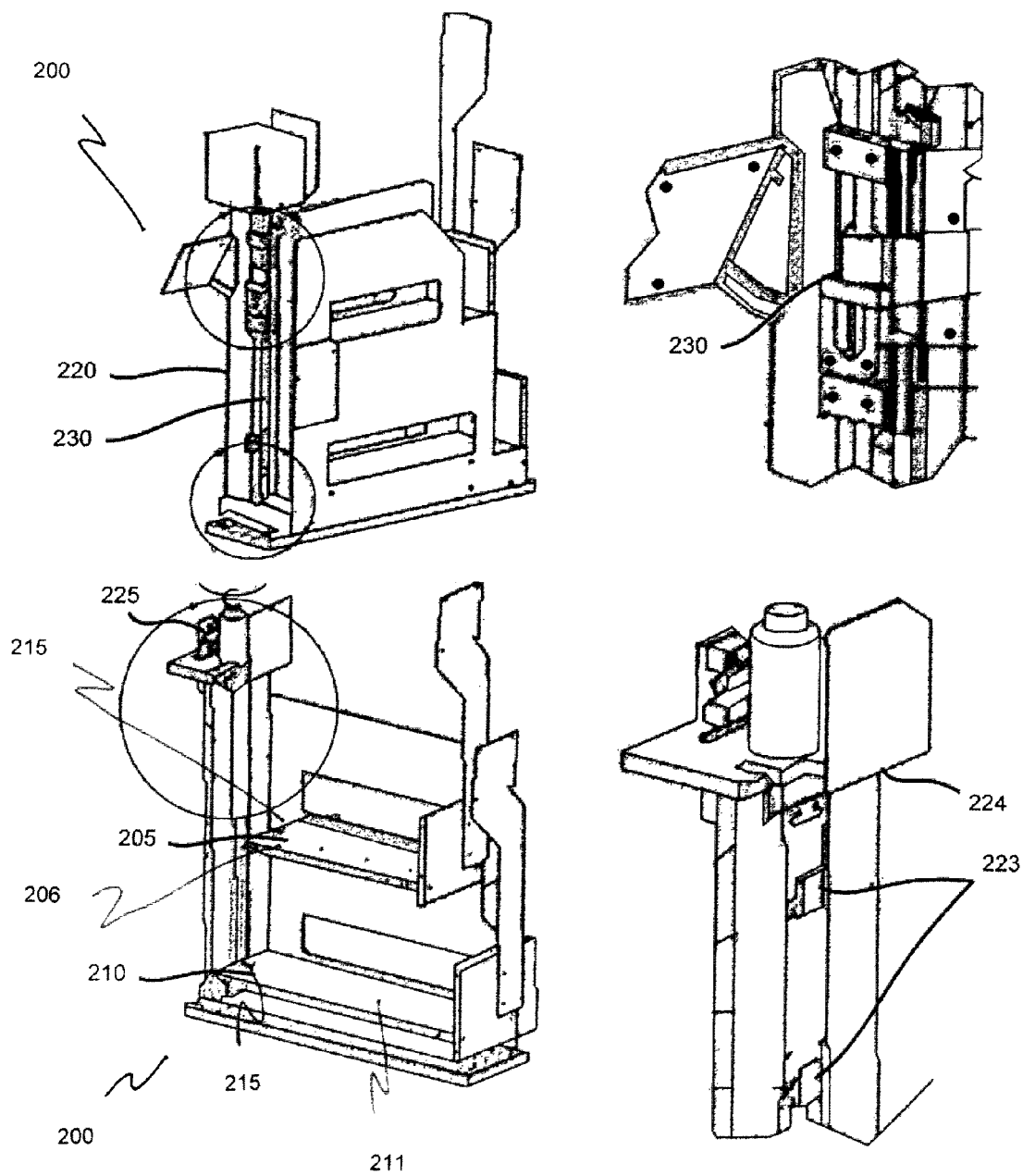
FIG. 3 is an simplified illustration of the elevator assembly.

An embodiment of cassette handler 200, the second component subsystem, as shown in FIG. 3 is a two-story system where the top level is comprised of upper rack 205 that serves as the input port for the cassette handler. The bottom level or lower rack 210 serves as the output port. Cassettes 100 are processed on a first-in first-out basis.

In an embodiment, an access door of the enclosure, or input port, allows admittance of cassettes 100 to upper rack 205. Upper rack 205 incorporates means to insure that cassette 100 is seated flush in the correct orientation. Upper rack 205 can accommodate a cue of up to 7 cassettes 100 for processing. Sensor 215 built into upper rack 205 can sense detectable device 115 installed in cassette 100, as previously described. In an embodiment, magnetic sensor 215 located under upper rack 205 detects magnet 115 integrated into cassette 100 thereby indicating the presence of cassette 100. There is one magnetic sensor 215 at each end of upper rack 205.

A means for transporting cassette 100 from the entrance to the exit of upper rack 205 is included. In an embodiment, upper conveyor belt 206, driven by motor (not shown), engages cassette 100 that was loaded at the entrance of upper rack 205, and moves it along upper rack 205 to the exit end.

Elevator assembly 220 is located at the exit end of the upper rack 205. In an embodiment, elevator assembly 220 consists of hooks that can engage the corresponding hook slots in cassette 100, which move up and down on spindle/lead-screw 230 driven by motor 225. The limits of travel of cassette 100 on elevator assembly 220 correspond to the location of upper rack 205 at one extreme and lower rack 210 at the other. Elevator assembly 220 may position cassette 100 anywhere within this range.

Lower rack 210 receives each cassette 100 after removal from elevator assembly 220. A sensor incorporated in the rack can sense the detectable device installed in cassette 100. In an embodiment, magnetic sensor 215 located under the rack detects magnet 115 integrated into cassette 100 indicating the presence of cassette 100. There is one magnetic sensor 215 at each end of lower rack 210.

A means for transporting cassette 100 from elevator assembly 220 to the exit of lower rack 210 is included. In an embodiment, lower conveyer belt 211, driven by motor (not shown), engages cassette 100 as it is released from the elevator assembly hooks, and moves it along lower rack 210 to the exit end and output port.

There are two data label readers, positioned respectively, at the input and output ports to read the cassette identification labels. In an embodiment these readers may be barcode readers.

Figure 4:
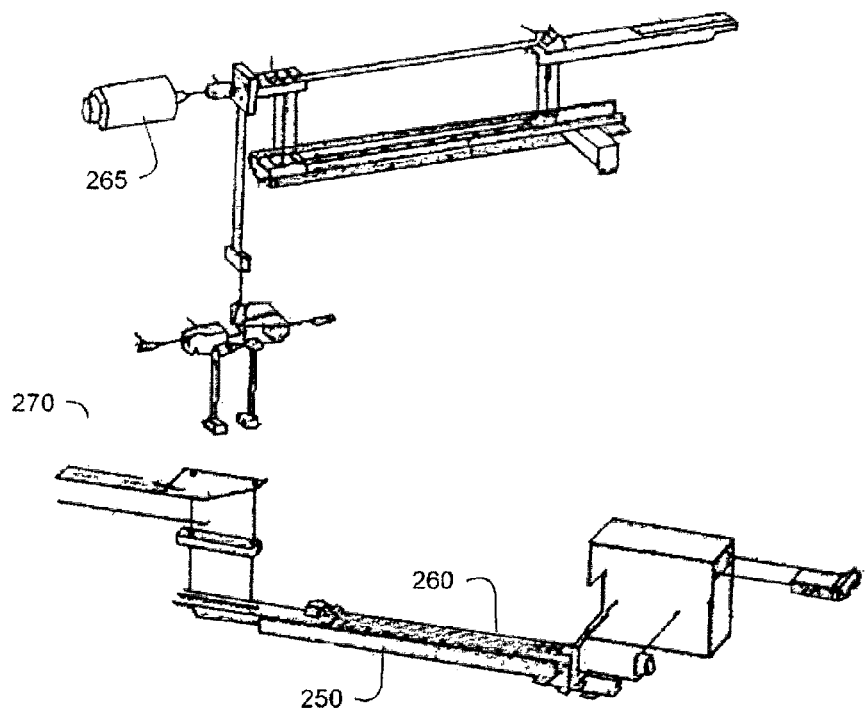
FIG. 4 shows several views of the feed arm assembly and actuator.
Figure 4:
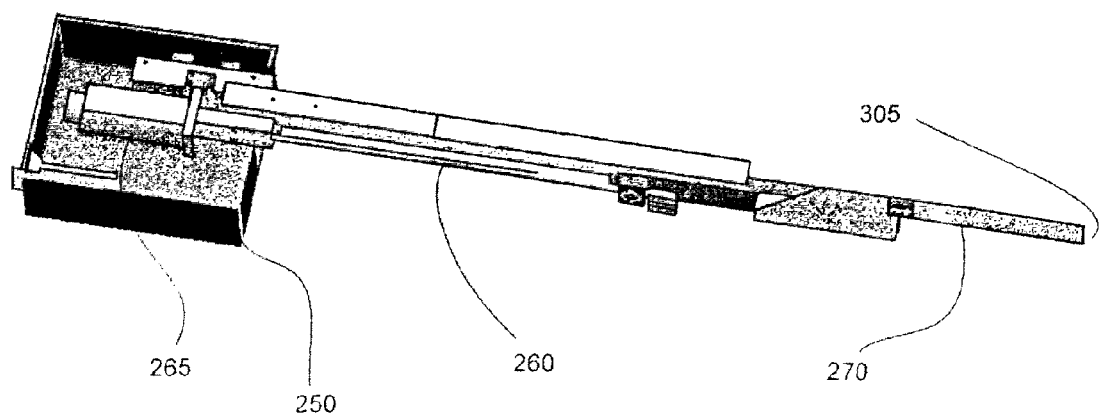

The third component subsystem, slide handler assembly 250 is shown in FIG. 4. Slide handler assembly 250 removes the slide from properly positioned cassette 100 and places it into slide holder 280. After the microscopic examination is completed, slide handler 250 removes the slide from slide holder 280 and returns it to the correct cassette slot.

Figure 5:
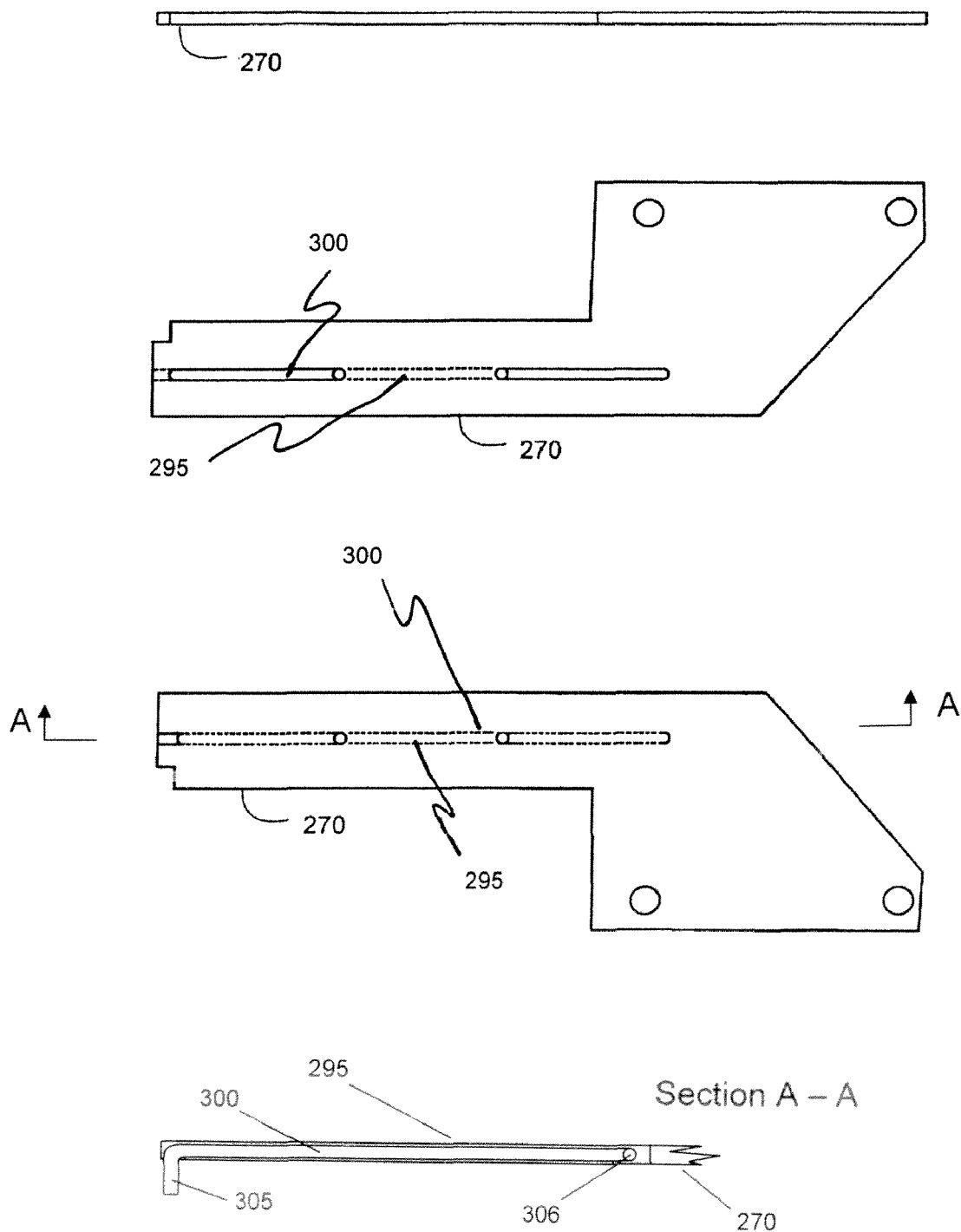
FIG. 5 shows side, top and bottom views of an embodiment of the feed arm.
Figure 6:
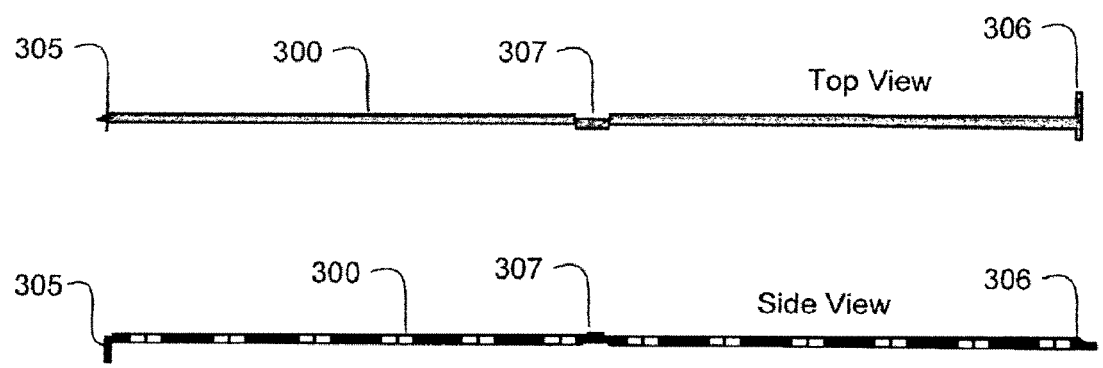
FIG. 6 shows a top and side view of an embodiment of the draw spring.

Slide handler assembly 250, as shown in FIG. 4, comprises feeder arm 270 that is mounted on lead-screw sub-assembly 260 driven by motor 265. An embodiment of feeder arm 270 is shown in FIG. 5. Lead-screw sub-assembly 260 can extend or retract feeder arm 270 while maintaining the arm in a horizontal position. Feeder arm 270 has a small channel 295 running through its length, which houses draw-out spring wire 300 as shown in FIG. 5. The two ends 305, 306 of the draw-out spring wire 300 are bent at 90 degrees orthogonal to the center length of the wire and to each other. The center of the length of the wire has small kink 307 (FIG. 6) lying in a plane 135 degrees relative to the planes formed by the bend at each end and the longitudinal axis of the center portion of the wire. Draw-out spring wire 300 is installed so that when forward end 305 of the wire is downward vertical, rear end 306 is horizontal and essentially co-planer with feeder arm 270. When draw-out spring wire 300 is made to rotate 90 degrees, forward end 305 becomes horizontal, and rear end 306 becomes downward vertical. Small kink 307 serves to prevent rotation of the wire beyond this 90-degree range.

The final component subsystem is the slide holder stage assembly. Slide holder stage 290 (FIG. 9) receives slide holder 280 (FIG. 9), containing the slide, from slide handler assembly 250 (FIG. 4) and positions the slide in the field of view of the microscope. Slide holder stage 290 can adjust the position of the slide along the X, Y, and Z Cartesian coordinate axis. Slide holder stage 290 is comprised of three orthogonally oriented linear actuators 310, 320, 330 that are mechanically coupled to provide the required displacement.

Figure 7:
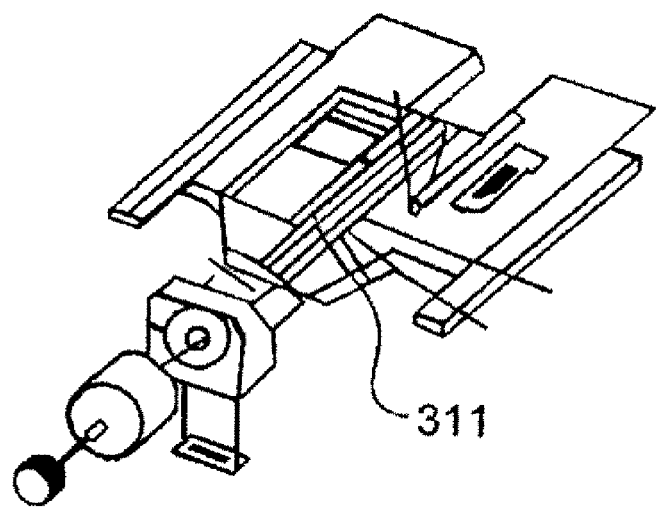
FIG. 7 shows an embodiment of the X axis slide stage.
Figure 8:
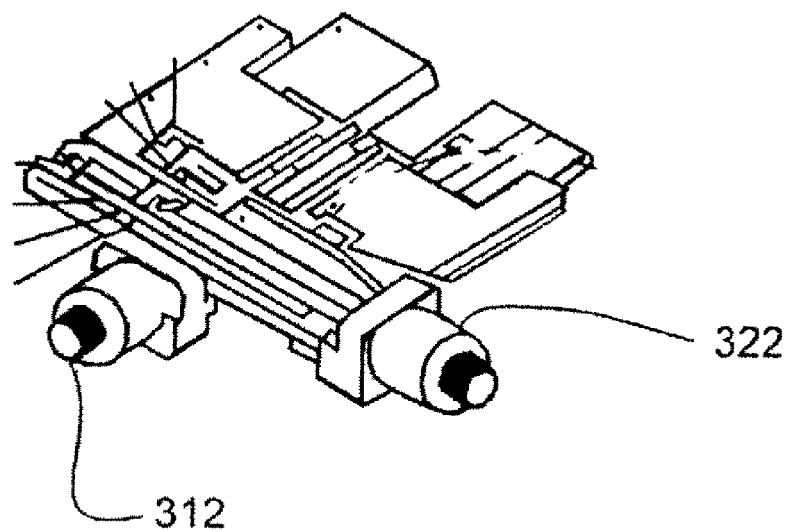
FIG. 8 shows an embodiment of the Y axis slide stage mounted on the X axis slide stage.

As shown in one embodiment as depicted in FIGS. 7-9, X-axis linear actuator 310 is lead-screw mechanism 311 driven by motor 312, which moves lead-screw nut along the X-axis. A Y-axis linear actuator 320 is mechanically connected to lead-screw nut of X-axis linear actuator 310 as shown in FIG. 8. Y-axis linear actuator 320 is driven by motor 322 that moves lead-screw nut along the Y-axis. Z-axis linear actuator 330 is mechanically connected to lead-screw nut of the Y-axis linear actuator as shown in FIG. 9. The Z-axis linear actuator is comprised of piezo-electric transducer 331 that converts an electrical control signal into a proportional linear displacement. Slide holder base 285 is mechanically fastened to piezo-electric transducer 331 so that the application of an electrical signal results in a linear displacement along Z-axis. Thus slide holder base 285 may be positioned in the three Cartesian coordinates.

While not depicted herein, motion along each of the Cartesian coordinates may each be accomplished by using a motor, such as a piezo motor, without need for lead screws. For example, three or more piezo motors may be employed, each effectuating movement of the slide holder in either the x, y or z plane. A control signal may be sent to each motor, or just to the motors to be effectuated into action. Such signal may be automatically generated pursuant to a control module which may include hardware and/or software components operatively configured to generate a predetermined movement of the slide over a period of time. Such control signal may also encompass manual input.

Each of the animated portions of the automated cassette and slide handling system may be instrumented to determine if a "Jam" has occurred. The instrumentation may, for example, include sensors which directly detect object displacement or, alternatively, sensors which measure actuator power supply Current. When a "jam" is detected, the system is safely brought to a halt and remedial actions are taken.

The operation of an embodiment automated cassette and slide handling system is now described.

Cassettes 100 are populated with specimen microscope slides. In addition, any necessary labeling of cassette 100 is affixed in the areas provided. Cassettes 100 are sequentially loaded through the access door at the input port onto upper rack 205. Upper rack 205 has the capacity to hold six cassettes 100 on the rack plus one loaded on elevator 220. In operation, the automated slide and cassette handling system continuously loads the cassettes which are manually loaded onto the upper rack. Sensors 215 at the input end of upper rack 205 detect the presence of cassettes 100 and upper conveyer belt 206 begins to move them toward elevator assembly 220. In addition, the sensors 215 may also interrogate the cassette mounted detectable devices and/or labels thereby reading identification data. The data provides unique identification of the cassette and, in combination with externally stored and executable software, description of the contained specimen slides.

When sensor 215 at the exit end of upper rack 205 detects cassette 100 that has been moved across upper rack 205 by upper conveyer belt 206, the speed of upper conveyer belt 206 is reduced, and cassette 100 is loaded onto elevator hooks 223. The elevator then lifts cassette 100 up to a home or zero position thereby applying force from end stop 224 (i.e. a screw) and locking cassette 100 to the elevator hooks. The position of cassette 100 relative to the elevator is thus precisely established. The elevator mechanism then lowers cassette 100 to the position necessary to access the selected microscope slide. Slide handler assembly 250 removes the selected slide from cassette 100.

The operation of slide handler assembly 250 is now described. Lead-screw sub-assembly 260 of slide handler assembly 250 extends feeder arm 270 into cassette 100, immediately above, and parallel to the surface of the slide to be examined. The forward edge of feeder arm 270, at this time, extends beyond the rear edge of the slide. Slide holder 280 is perpendicularly slid under feeder arm 270, immediately in front of the open end of cassette 100. As slide holder 280 moves, it contacts downwardly vertical rear end 306 (i.e. the end outside cassette 100) of the draw-out spring wire causing the wire to rotate 90 degrees to the horizontal position. The rotation of the wire causes forward end 305 (i.e. the end which is inserted into cassette 100) of draw-out spring wire 300 to also rotate 90 degrees to the downward vertical position. Slide handler assembly 250 withdraws feeder arm 270 from cassette 100. Since forward end 305 of the draw-out spring wire is now in the downward vertical position, the wire makes contact with the back edge of the slide and pulls it out of its cassette slot onto slide holder 280 which is installed in slide holder stage 290. Slide holder 280 securely grips the slide and transports it to the microscope's optical path for examination.

Slide holder stage 290 positions and re-positions the slide under the microscope, as required, with the X and Y coordinate position controlled by respective motor driven linear actuators 310, 320 and the Z coordinate position controlled by piezo-electric transducer 331.

Having completed the microscopic examination of the slide, slide holder 280 is perpendicularly slid back to its location in front of cassette 100. In the process of sliding slide holder 280 into place, slide holder 280 contacts vertically downward protruding forward end 305 of draw-out spring wire 306 and rotates it to the horizontal position. The 90-degree rotation causes rear end 306 of draw-out spring wire 300 to rotate from the horizontal position to the downwardly vertical position. Slide handler assembly 250 extends, and rear end 306 of the draw-out spring wire 300 contacts the edge of the slide and pushes the slide back into the appropriate slot in cassette 100. Slide handler assembly 250 retracts feeder arm 270 and the process is complete.

Elevator assembly 220 moves cassette 100 to the next slide position and the process is repeated. When all of the slides in cassette 100 have been examined, elevator assembly 220 moves cassette 100 to lower rack 210 where cassette 100 is decoupled from elevator hooks 223. Sensor 215 on lower rack 210 detects the presence of cassette 100, and lower conveyer belt 211 transports cassette 100 to the exit of lower rack 210.

After microscopic examination, the removed slide is reinserted into its appropriate cassette slot 110. Elevator assembly 220 repositions cassette 100 so that the next slide, as determined by the protocol, is correctly positioned for access. The slide access and replacement process is repeated until each of the required slides has been examined.

When all of the slides have been examined, elevator assembly 220 lowers cassette 100 to the level of lower rack 210 where cassette 100 is released from elevator hooks 223.

STATEMENT REGARDING PREFERRED EMBODIMENTS

While the invention has been described with respect to preferred embodiments, those skilled in the art will readily appreciate that various changes and/or modifications can be made to the invention without departing from the spirit or scope of the invention as defined by the appended claims. All documents cited herein are incorporated by reference herein where appropriate for teachings of additional or alternative details, features and/or technical background.

What is claimed is:

1. A mechanism comprising:
    a feed arm containing a longitudinal channel therethrough;
    a draw-out spring wire, defining a longitudinal axis, and having a first end and a second end, said first end and said second end each bent orthogonal to one another and to said longitudinal axis, said draw-out spring wire being positioned in said longitudinal channel in said feed arm such that said first end and said second end perpendicularly protrudes from said longitudinal channel and said longitudinal draw-out spring wire is operatively configured in said longitudinal channel such that the draw-out spring wire is rotatable therein, allowing for each bent end to change orientation with respect to said feed arm.

2. A computerized method for automatically handling microscope slides comprising the steps of:
    detecting said cassette containing a plurality of microscope slides at an input port by way of a detectable device affixed to said cassette;
    sequentially removing and replacing each of said plurality of microscope slides wherein each said removing and replacing comprises:
    a) positioning said cassette to provide access to one of said plurality of microscope slides;
    b) extending a feeder arm, comprising a draw-out spring wire having a forward end and a rear end, into said cassette immediately above and parallel to surface of the microscope slide desired to be removed;
    c) moving a slide holder under said feeder arm whereby said slide holder contacts said rear end of said draw-out spring wire thereby causing said draw-out spring wire to rotate by approximately 90 degrees;
    d) withdrawing said feeder arm from said cassette whereby forward end of said draw-out spring wire contacts said microscope slide thereby causing said slide to be withdrawn from said cassette and placing said microscope slide onto said slide holder;
    e) automatically removing said microscope slide from said slide holder and returning said microscope slide to said cassette.

* * * * *